United States Patent [19]

Monji et al.

[11] Patent Number: 5,206,136
[45] Date of Patent: Apr. 27, 1993

[54] RAPID MEMBRANE AFFINITY CONCENTRATION ASSAYS

[75] Inventors: Nobuo Monji; Carol-Ann Cole, both of Seattle, Wash.

[73] Assignee: Genetic Systems Corporation, Redmond, Wash.

[21] Appl. No.: 925,311

[22] Filed: Jul. 31, 1992

Related U.S. Application Data

[63] Continuation of Ser. No. 590,886, Oct. 1, 1990, which is a continuation-in-part of Ser. No. 108,485, Oct. 20, 1987, which is a continuation-in-part of Ser. No. 932,656, Nov. 19, 1986, abandoned.

[51] Int. Cl.$^5$ .................... G01N 33/538; C12Q 1/00
[52] U.S. Cl. ............................ 435/5; 435/7.1; 435/7.5; 435/7.92; 435/7.93; 435/7.94; 435/7.95; 435/180; 435/803; 435/971; 435/974; 436/501; 436/539; 436/810
[58] Field of Search .................... 435/5, 174, 180, 971, 435/974; 436/539, 541, 162, 174, 178, 810

[56] References Cited

U.S. PATENT DOCUMENTS

| | | | |
|---|---|---|---|
| 4,312,944 | 1/1982 | Mattiasson | 435/7.92 |
| 4,418,152 | 11/1983 | Hosaka et al. | 435/7.36 |
| 4,451,568 | 5/1984 | Schneider et al. | 435/174 |
| 4,455,370 | 6/1984 | Bartlesman | 435/180 |
| 4,504,585 | 3/1985 | Reynolds . | |
| 4,520,113 | 5/1985 | Gallo et al. | 435/974 |
| 4,530,900 | 6/1985 | Marshall | 436/539 |
| 4,624,783 | 12/1986 | Cosand | 435/961 |
| 4,632,901 | 12/1986 | Valkirs et al. . | |
| 4,649,105 | 3/1987 | Kasahara et al. . | |
| 4,666,866 | 5/1987 | Krauth . | |
| 4,711,840 | 12/1987 | Nowinski et al. | 436/539 |
| 4,727,019 | 2/1988 | Valkirs et al. . | |
| 4,737,453 | 4/1988 | Primus | 435/5 |
| 4,742,011 | 3/1988 | Blake et al. . | |
| 4,780,409 | 10/1988 | Monji et al. | 435/5 |
| 4,839,288 | 6/1989 | Montagnier | 435/5 |
| 4,978,614 | 12/1990 | Bronstein | 435/6 |

FOREIGN PATENT DOCUMENTS

| | | |
|---|---|---|
| 011837 | 6/1980 | European Pat. Off. . |
| 028132 | 5/1981 | European Pat. Off. . |
| 094777 | 11/1983 | European Pat. Off. . |
| 206302 | 12/1986 | European Pat. Off. . |
| 211229 | 2/1987 | European Pat. Off. . |
| 2476125 | 8/1981 | Fed. Rep. of Germany . |
| 2028091 | 3/1980 | United Kingdom . |

OTHER PUBLICATIONS

Oellerich, *J. Clin. Chem. Clin. Biochem.* 22:895–904 (1984).
Cole et al., *Am. Chem. Soc.* 17:245–254 (1987).
Monji et al., *Biochem. Biophys. Res. Com.* 172:652–660 (1990).

*Primary Examiner*—Christine M. Nucker
*Assistant Examiner*—Chris Dubrule
*Attorney, Agent, or Firm*—Townsend and Townsend

[57] ABSTRACT

Rapid assays for analytes of interest in a fluid sample utilize a first conjugate of a labelled reactant that specifically binds to the analyte, and a second conjugate that binds to the analyte coupled to a polymer that has an affinity for a selected solid phase. The reaction components are incubated briefly, then contacted with the selected solid phase and the labelled components determined. Optional wash steps provide for enhanced sensitivity and specificity. When the analyte of interest is an antibody to HIV, the first reactant may be a synthetic, recombinant or native HIV antigen, and the second reactant may be protein A or an anti-immunoglobulin.

21 Claims, 4 Drawing Sheets

RAPID MEMBRANE AFFINITY CONCENTRATION ASSAYS

CROSS-REFERENCE TO RELATED APPLICATIONS

This is a continuation of application Ser. No. 07/590,886 filed Oct. 1, 1990, now abandoned, which is a continuation-in-part of USSN 07/108,485, filed Oct. 20, 1987, which itself is a continuation-in-part of USSN 06/932,656, filed Nov. 19, 1986 and now abandoned.

BACKGROUND OF THE INVENTION

Immunoassays have found widespread application in the field of clinical diagnostics for the detection and measurement of antigens, antibodies, drugs, vitamins, hormones, metabolites and other substances of interest in biological and non-biological fluids. Typically, these analytes occur in micromolar ($20^{-6}$ M) or less concentration.

With the discovery of the human immunodeficiency virus (HIV) and its role as the cause of AIDS well established, much effort has focused on the development of immunoassays for antibodies to HIV viral components in biological fluids. Other assays have been designed to detect HIV viral antigens. The most commonly employed antibody screening assay is an enzyme-linked immunoadsorbent assay (ELISA) using whole virus lysates adsorbed to a solid phase, such as a microtiter well or bead. These assays typically involve long incubation periods and thus require as much as 3–4 hours to perform. More rapid tests have been developed based on agglutination of microparticles coated with viral proteins, but these assays are sometimes difficult to interpret and present problems of sensitivity and specificity.

Immunoassays such as ELISAs are referred to as heterogeneous because the signal emitted by a bound labelled reactant is indistinguishable from the signal emitted by free labelled reactant and thus a separation step is required to distinguish between the two. These assays typically employ at least one reactant immobilized on a solid phase to effect such separation. Solids used to immobilize reactants in immunoassays have included controlled pore glass and preformed polymers, such as polyvinyls, polyacrylamides, polydextrans, and polystyrenes. Numerous separation methods are known in the art and have been used in heterogeneous immunoassays. These include centrifugation, microfiltration, affinity chromatography, and gel-permeation chromatography. Since the kinetics of reaction between an immobilized antibody (or antigen) and its binding site tend to be slower than the kinetics of the same reaction occurring in solution, long incubation times are frequently required. When the multiple wash steps often needed are considered, it can be appreciated that heterogeneous assays tend to be time-consuming and labor-intensive.

There is a need in the art, then, for an HIV immunoassay which is highly sensitive, has fast-reaction kinetics, and which is readily amenable for use in efficiently detecting the presence of a variety of HIV analytes within a home or clinical setting. The present invention fulfills this need and further provides other related advantages.

SUMMARY OF THE INVENTION

The present invention discloses methods for rapidly determining the presence and/or concentration of an analyte in a fluid sample. The method generally comprises incubating a sample suspected of containing an analyte of interest with (i) a conjugate of a first reactant that specifically binds with the analyte conjugated to a label capable of providing a detectable signal, and (ii) a second conjugate which comprises a second reactant that binds to the analyte and a polymer which has an affinity for and selectively binds to a selected solid phase. The reaction mixture is contacted with the solid phase and the amount of label bound to the solid phase measured, thereby determining the presence and/or concentration of the analyte. The method may optionally include washing the solid phase after the reaction mixture is contacted with the solid phase to remove nonspecifically bound label.

The analyte to be determined may be antigen or antibody. In certain preferred embodiments the analyte will be antigens of or antibodies to HIV-1, HIV-2, HTLV-I, HTLV-II, hepatitis B virus, or non-A, non-B hepatitis viruses. When the analyte of interest is an antibody, the reactant which binds to the antibodies may be viral lysates, purified viral proteins (purified authentic proteins or produced by recombinant DNA techniques), or synthetic peptides. When the analyte is an antibody, the second reactant may be, e.g., protein A or an anti-immunoglobulin, such as anti-human immunoglobulin when human antibodies are sought to be detected.

The polymer to which the second reactant is bound can be one characterized by a critical solution temperature. Particularly preferred are polymers of N-alkylacrylamides, N-arylacrylamides, alkyl acrylates and combinations thereof. Further, the polymer can be a copolymer or terpolymer formed from selected monomers, such as N-isopropylacrylamide monomers and N-acryloxysuccinimide monomers copolymerized with a variety of other monomers. A particularly preferred terpolymer is formed from N-isopropylacrylamide, N-acryloxysuccinimide and N-n-butylacrylamide. A preferred non-hydrophobic solid phase is cellulose acetate when the polymer is comprised of N-isopropylacrylamide or its derivatives.

The reporter which is used to provide a detectable signal is conjugated to a reactant that binds an analyte of interest. The reporters include enzymes, fluorophores, radioisotopes, luminescers, particles, etc. Particularly preferred among the luminescers are chemiluminescers, such as 3-(2'-spiroadamantane)-4-methoxy-4-(3'-phosphoryloxy)phenyl-1,2-dioxetane (AMPPD), and 3-(2'-spiroadamantane)-4-methoxy-4-(3''-β-D-galactopyranosyloxy) phenyl-1,2-dioxetane (AMPGD), among others.

DESCRIPTION OF THE PREFERRED EMBODIMENT

Figure 1:
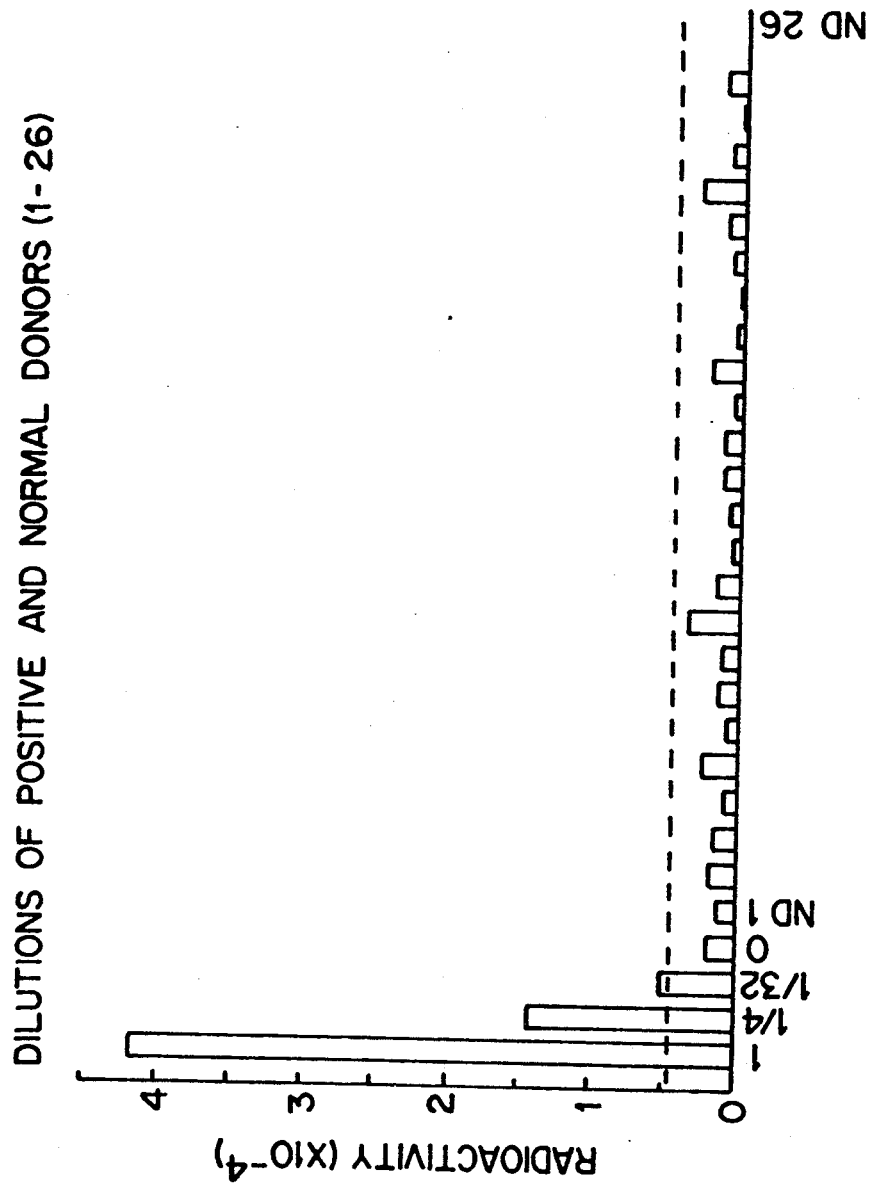
FIG. 1 depicts the results of assays for antibodies to HIV-1 in dilutions of a positive control serum and in 26 normal donors.

In the present application, polymers are used in cooperation with selected solid phases to detect the presence and/or concentration of analytes of interest. The analytes may be antibodies which bind to antigens, or the analytes may be antigens. In other embodiments the analytes may be specific nucleic acid sequences, which are recognized and specifically bound by complementary oligonucleotides. The present invention may be used for detecting the presence of analytes in a fluid sample, usually biological fluids, although other fluids are possible. Biological fluids include, e.g., blood, blood serum, blood plasma, saliva, sputum, urine, cerebrospinal fluid, amniotic fluid, cells and tissues and extracts thereof, and viral cultures and their extracts. Depending on the assay format and the binding reagents, the present invention provides an extremely rapid test that is both sensitive and specific.

The separation of complexes of analyte-reactant from a reaction mixture is achieved by utilizing the affinity of certain polymer compositions for various solid phases. A variety of polymers may be useful within the present invention, depending in part upon their affinity for a particular solid phase. Suitable synthetic polymers may be formed from a single monomeric species (homopolymers) or preferably from a mixture of different monomers (copolymers). Representative classes of polymers useful within the present invention include those composed of N-alkylacrylamides, N-arylacrylamides, alkyl acrylates, aryl acrylates and combinations thereof.

In a particularly preferred embodiment of the present invention, conjugates of reactants with polymers exhibiting a lower critical solution temperature (polymer-reactant conjugates) are utilized. Certain water-soluble polymers are known to precipitate when a critical solution temperature is reached (Molyneux, *Water Soluble Synthetic Polymers: Properties and Behavior*, CRC Press, Boca Raton, Fla., 1983). The majority of polymers exhibit de-mixing behavior (phase separation) upon cooling. However, certain polymers exhibit de-mixing behavior (phase separation) upon heating and the temperature at which de-mixing occurs is referred to as the lower critical solution temperature (LCST).

Among polymers which exhibit a lower critical solution temperature are the following: polyvinyl methylether (PVME), polyvinylmethyl oxazolidone (PVMO), polymethacrylic acid (PMAA), poly-N-isopropylacrylamide (PNIPAAm), hydroxypropyl cellulose (HPC), and methyl cellulose (MC). (Franks, in C.A. Finch, ed., *Chemistry and Technology of Water-Soluble Polymers*, New York, Plenum Press, 1983, p. 157). Any polymer or copolymer or monomers thereof, be they naturally occurring, synthetic, or semi-synthetic, which is capable of selectively binding to a particular solid phase following conjugation to a reactant can be used in the immunoassays of the present invention.

Particularly preferred are polymers or monomers of N-isopropylacrylamide and derivatives thereof. In addition, several monomers may be copolymerized with N-isopropylacrylamide monomers in order to produce particularly desirable copolymers. For instance, such monomers include N-n-butylacrylamide monomers and N-acryloxysuccinimide monomers. Two preferred copolymers are N-isopropylacrylamide: N-acryloxysuccinimide, 100:2.5 (A-poly 5); and N-isopropylacrylamide: N-acryloxysuccinimide: N-n-butylacrylamide, 60:2.5:40 (A-poly 32, also referred to herein as A-poly 47). Suitable acrylate monomers include n-amyl acrylate, iso-amyl acrylate, n-octyl acrylate, methyl acrylate, ethyl acrylate, hexadecyl acrylate and 3,5,5-trimethylhexyl acrylate. Other suitable acrylamide monomers include N-tert-butylacrylamide, N-decylacrylamide, N-tert-octylacrylamide, N-benzylacrylamide, N-iso-butoxymethylacrylamide, and diacetone acrylamide.

A reporter-reactant conjugate is employed in the assay, where the reactant specifically binds to the analyte of interest. Selection of the reactant is dependent on the analyte and assay mode, but typically, the reactant is an antibody or an antigen; however, other reactants are known in the art, including, for example, oligonucleotides, lectins, receptors, transport proteins, and non-immunoglobulin antibody-binding proteins, such as staphylococcal protein A and/or protein G. Where the reactant is an oligonucleotide probe (single-stranded or double stranded DNA or RNA), a variety of methods of synthesizing nucleic acid sequences complementary in whole or in part to given sequences of the analyte of interest are known in the art. Where the reactant is an antibody, either monoclonal or polyclonal antibodies can be used. Prior to conjugation to the reporter, the antibodies will, in general, be at least partially purified by methods well known in the art. If necessary, the reactant can be coupled to a carrier, such as the soluble proteins bovine serum albumin, ovalbumin, thyroglobulin, and the like.

In certain embodiments described herein, the analytes of interest are antibodies which bind to HIV antigens, including antigens of HIV-1 and HIV-2. In these cases the reactants are synthetic HIV peptides (see, e.g., U.S. Pat. No. 4,629,783, incorporated herein by reference), recombinant HIV proteins, and/or HIV lysate proteins which bind to the anti-HIV antibodies, particularly those antibodies produced in an individual as a result of vaccination and/or infection by the virus. In other embodiments the analytes of interest are antibodies to, or antigens of, other retroviruses such as HTLV-I and HTLV-II, or the hepatitis A and B viruses, including hepatitis B surface antigen, and non-A non-B hepatitis viruses, as described in, e.g., EPO publication EP 318,216.

The reporter (label) which is conjugated to the first reactant can be chosen from any of those known in the art, including enzymes, fluorophores, radioisotopes, luminescers, dye particles, etc. Some suitable fluorophores include fluorescein, rhodamine, phycoerythrin, phycocyanin, and nile blue. Preferred luminescers include chemiluminescers, such as 3-(2'-spiroadamantane)-4-methoxy-4-(3'-phosphoryloxy)phenyl1,2-dioxetane (AMPPD), 3-(2'-spiroadamantane)-4-methoxy-4-(3''-β-D-galactopyranosyloxy) phenyl-1,2-dioxetane (AMPGD), luminol, isoluminol, or firefly luciferin. Among preferred enzymes are horseradish peroxidase (HRP), β-galactosidase (β-GAL), glucose oxidase, urease, β-lactamase, and alkaline phosphatase (AP). When the reporter is an enzyme, the step of measuring may include exposing the bound complex to substrate and incubating for color, fluorescence or luminescence development. It will be evident to one skilled in the art that the particular substrate utilized will be dependent upon the enzyme chosen. Methods for coupling the reporter to the first reactant are dependent on the reporter and reactant chosen, but such methods are generally known to the skilled artisan.

In addition to a reporter-reactant conjugate, a polymer-reactant conjugate is generally employed in the assays of the present invention. The polymer should have an affinity for a selected solid phase, as described above. The reactant can be selected from any of those previously described for the reporter-reactant conjugate. The second reactant of the assay should be reactive with a site on the analyte which preferably is different from the site recognized by the first reactant, so as to not interfere in the binding of the first reactant-label to the analyte, but in some instances the first and second reactants may bind to the same site on the analyte. In certain embodiments described herein, when the analyte of interest in a sample is an antibody, the reactant which is coupled to the polymer binds the analyte in a manner that is not dependent on the binding specificity of the analyte antibody. Such reactants include, e.g., protein A, protein G, and anti-immunoglobulin antibodies.

The polymer can be preformed (pre-polymerized) and the reactant conjugated to the preformed polymer by conventional chemistry. For example, an activated ester of the polymer can be conjugated to reactive groups on the reactant. Alternatively, the reactant can be conjugated to a monomer and then copolymerized with additional monomers to yield a copolymer-reactant.

Purification of the polymer-reactant conjugate can be accomplished by any of a variety of methods well known in the art. For example, the conjugate can be purified by gel-permeation chromatography. Alternatively, it can be purified by serial precipitation of the polymer-reactant conjugate. If the latter method is used, care must be taken to ensure that the reactant is not denatured.

Gel-permeation chromatography and serial precipitation will suffice to remove free antibody from antibody-conjugated polymer but will not remove free polymer from the mixture. Separation of free polymer from antibody-conjugated polymer can be accomplished by chromatography on hydroxylapatite (HAP), a protein A affinity column, an antibody-specific affinity column, and the like. The free polymer will pass through the column at conditions under which the antibody-conjugated polymer will bind to the column. The conjugate can subsequently be eluted by changing the ionic strength of the buffer in which chromatography is performed.

In general, it is preferred that the antigen/antibody (or other specific binding) reaction take place at temperatures between about 0° C. and 55° C., more often between 22° C. and 45° C. In many instances, specific binding reactions can be enhanced by raising the temperature to between 37° C. and 45° C.

Separation of free from specifically bound reporter-reactant conjugate is effected by contacting the ternary complex formed which consists of polymer-reactant, analyte and reporter-reactant with a solid phase capable of selectively binding the polymer-reactant and polymer-reactant/analyte/ reporter-reactant complex. Any free reporter-reactant conjugate that attaches nonselectively to the solid phase may be removed by washing the solid phase.

A variety of non-hydrophobic solid phases may be utilized within the methods described herein, including esters of cellulose, such as cellulose acetate, depending upon the particular polymers selected.

A particularly preferred solid phase for use herein is a cellulose acetate membrane. One advantage of this particular membrane is that it has very low nonspecific protein binding properties, which can be further minimized by treatment with bovine serum albumin (BSA). In addition, it has been determined that there is minimal interference by proteins and mild detergents to the binding of the complex to this membrane. When cellulose acetate is chosen as the solid phase, preferred polymers include poly-N-isopropylacrylamide or its derivatives. It is preferable when performing the immunoassay using this particular combination of polymer and solid phase to maintain a temperature above the LCST of the polymer.

Although it is preferable to utilize poly-N-isopropylacrylamide or its derivatives in combination with cellulose acetate, it will be evident that a variety of other polymers may be suitable for use with this membrane. Generally, any polymer which is capable of selectively binding to the cellulose acetate membrane may be utilized. The affinity of a particular polymer for cellulose acetate or another solid phase may be readily determined, for example, through use of a relatively simple screening procedure. The polymer may be tested alone or conjugated to a reactant. Polymer, labeled with a radioactive tag or unlabeled, is admixed with the solid phase. If unlabeled, the flow through the solid phase is monitored for UV absorbance at 214 nm and the quantity of polymer adsorbed determined. If radioactively tagged, e.g., $^{125}I$, the solid phase is counted in a gamma counter, and again the quantity of polymer adsorbed is determined. The polymer, copolymer, or conjugates thereof should have an affinity of at least $10^{-2}M$, more commonly at least $10^{-6}M$, and even more preferred, $10^{-10}M$, under the actual assay condition.

The step of contacting the solid phase with the reaction mixture containing the ternary complex may be accomplished in a variety of ways. Particularly preferred methods include filtering the reaction mixture through the solid phase or dipping the solid phase into the reaction mixture. By filtration is meant to include fluid movement by means of capillary action, wicking, pressure-force, vacuum, gravity, etc. The present invention is amenable to a dipstick assay format, since the specific signal bound to the membrane is an affinity phenomenon and is not easily removed. In addition, no prior modification or treatment of the membrane is necessary in order to achieve this result.

Alternatively, a polymer-reactant conjugate may be first contacted with a solid phase capable of selectively binding with the polymer, such that the polymer is bound to the solid phase. The solid phase having polymer bound thereto is then contacted with a biological fluid sample suspected of containing an analyte of interest. Subsequently, the solid phase having polymer-reactant/analyte complexes bound thereto is contacted with a reporter-reactant conjugate capable of specifically binding with the analyte, such that specific binding occurs. The reporter is adapted to generate a signal that is quantitatively related to the presence and/or concentration of the analyte, allowing one to measure the amount of reporter activity in the bound complex and therefrom determine the presence and/or concentration of the analyte.

The immunoassays of the present invention can be performed in any of several configurations. These can include competitive, sandwich, and non-competitive immunoassay configurations. In every case, the analyte of interest can be an antigen or an antibody. In every case, the reactant (i.e., antigen or antibody) can be conjugated to either the polymer or to the reporter. The various possible configurations in which immunoassays can be performed are reviewed extensively in *Enzyme Immunoassay*. E.T. Maggio, ed., CRC Press, Boca Raton, Fla. (1980); 'Practice and Theory of Enzyme Immunoassays,' P. Tijssen, *Laboratory Technicues in Biochemistry and Molecular Biology*, Elsevier Science Publishers B.V. Amsterdam (1985); *Enzyme-Mediated Immunoassay*, T.T. Ngo and H.M. Henhoff, Plenum Press, New York (1985), and in numerous other publications.

In other embodiments, a 'common-capture' assay format can be employed. In this method, one member of a common-capture binding pair, such as avidin of the avidin-biotin binding pair, is conjugated to the polymer which has a specific affinity for a selected solid phase, thereby forming a common-capture reagent. The analyte of interest in the sample is bound by a first reactant that specifically binds the analyte, wherein the first reactant is conjugated to a label capable of providing a detectable signal. Another conjugate, which comprises a second reactant that binds to the analyte and the second member of the common-capture binding pair (i.e., biotin in this example), is added to the sample reaction mixture containing the analyte of interest. After a period of incubation under conditions conducive to specific complex formation, the polymer-avidin conjugate is added, the solution briefly mixed, and then is contacted with the selected solid phase. The amount of label bound to the solid phase is measured, thereby determining the presence and/or concentration of the analyte.

Advantages of the common-capture format include (1) a single polymer-selected solid phase combination and a generic capture conjugate (e.g., avidin-polymer conjugate) that can be used for a variety of different assays, (2) the second reactant need only be conjugated to the capture reagent's binding member, e.g., biotin, which makes the preparation of the second reactant conjugate simpler and easier; and (3) the time necessary for the polymer to contact the assay mixture is minimized, making the nonspecific background signal of the assay very low.

Multiple analyses for different HIV antigens or antibodies to different antigenic determinants of the same or different HIV antigens, e.g., envelope, gag, or polymerase proteins and the like, or to distinguish between antigens/antibodies of HIV-1 and HIV-2 in the same sample, can be performed on a sample by choosing a variety of reporters, each reporter having a different specific binding partner conjugated thereto. The ternary complexes bound to a solid phase would then be analyzed for the presence of each reporter. Particularly preferred reporters in this regard include, e.g., fluorescein and rhodamine, enzymes such as horseradish peroxidase, β-galactosidase, alkaline phosphatase, etc.

As noted above, there are a variety of alternatives to measuring the amount of reporter activity in the complex bound to the solid phase or free reporter in solution. In one such alternative, the entire bound complex is eluted from the solid phase, wherein agents for disrupting either hydrophobic interactions or hydrogen bonding, such as 0.2% sodium dodecyl sulfate or 4M potassium thiocyanate, can be used, while in another alternative only the reporter-reactant conjugate portion is eluted from the solid phase. It will be evident to one skilled in the art that the conditions required to release the reporter-reactant portion are dependent upon the reactant chosen.

Kits can also be supplied for use with the compositions and methods of the present invention for the detection and/or concentration of analytes of interest. Thus, the reporter-reactant conjugate and the reactant-polymer conjugate may be provided in a container, in some instances in lyophilized form, either alone or in conjunction with additional reagents, such as buffers, stabilizers, biocides, inert proteins, e.g., serum albumin or the like. Frequently it will be desirable to include an inert extender or excipient to dilute the active ingredients, where the excipient may be present in from about 1 to 99% of the total composition. In some instances the active ingredients, such as antibodies or antigens, may be supplied unconjugated. The selected solid phases for which the polymer has affinity can also be supplied as part of the kit, and may take the form of filters, dipsticks, coated beads adn the like. The kit may also contain instructions for using the components in the methods described herein.

The following examples are offered by way of illustration and not by way of limitation.

EXAMPLE I

Rapid RIA Procedure for Detecting Antibodies to HIV-1

The following experimental example describes a rapid procedure for detecting antibodies to HIV-1 which is both extremely sensitive and specific. Radioactive $^{125}$I was used as a signal generator and was conjugated to a synthetic peptide which immunologically mimics an HIV gp41 antigen, synthetic peptide 39GC described in more detail in pending application USSN 07/532,429, incorporated herein by reference. The peptide 39GC was first conjugated to BSA as a soluble carrier to form a peptide-BSA conjugate. This peptide-BSA conjugate was then labelled with $^{125}$I to form the signal conjugate. The signal conjugate was then reacted wtih a fluid sample suspected of containing antibodies to HIV, quickly followed by the addition of teh capture conjugate, in this example protein A conjugated to the polymer A-poly 47. Following a brief incubation period, the raction mixture was passed through a cellulose acetate membrane filter. By virtue of the specific affinity of the polymer for hte cellulose actetate, the ternary immune complexes are bound tightly to the filter. Following a wash period, teh signal on the membrane was then determined.

Preparation of Signal Conjugate, $^{125}$I-BSA-Peptide 39GC

To conjugate BSA to Peptide 39GC, the BSA was first derivatized with sulfo-succinimidyl 4-(N-maleimidomethyl) cyclohexane-1-carboxylate (sulfo-SMCC). A solution of BSA (30 mg/1.5 ml. of 0.1M HEPES, pH 7.0) was combined with 5 mg of sulfo-SMCC dissolved in 150 μl of dry dimethylformamide (DMF) and incubated for 30 minutes at room temp. The mixture was then applied to a Sephadex ® G-25 column (1×30 cm) equilibrated with 0.1M 4-(2-hydroxyethyl)-1-piperazineethanesulfonic acid (HEPES) buffer, pH 7.0, and then eluted with the same HEPES buffer. The main protein peak from the elution was collected and pooled.

The BSA-SMCC preparation was then conjugated to Peptide 39GC. To a solution of 8 mg BSA-SMCC in 1.5 ml of 0.1M HEPES, pH 7.0, in a glass tube, was added 8 mg of Peptide 39GC dissolved in 2 ml of distilled water. The peptide 39GC was prepared according to the protocol set forth in copending U.S. Ser. No. 07/532,429. The resulting milky-colored mixture was incubated for two hours at room temp., and then 0.4 ml of glacial acetic acid added to produce a clear solution of about 10% acetic acid. The solution was then applied to a Sephadex® G-75 column (1.5×40 cm) equilibrated with 20% acetic acid and eluted with the same 20% acetic acid solution at a rate of 1.3 ml/fraction. The $A_{280}$ was determined for each fraction and the first protein peak, the BSA-Peptide 39GC (EC protected), was collected and fractions pooled. Five volumes of distilled water were added to the pooled BSA-39GC conjugate, which was then frozen using dry ice/acetone and lyophilized. The lyophilized material was stored at 4° C.

To deprotect and oxidize the thiol groups of the conjugated 39GC peptide, 8 mg of the lyophilized BSA-Peptide 39GC (EC protected) mixture was dissolved in 1.5 ml of distilled water, and then 1.5 ml of 0.5N NaOH were added and the mixture incubated for three minutes at room temp. After the incubation period, 12 ml of 0.25M HEPES, pH 7.5, were added and mixed, followed by the addition of 150 µg of potassium ferricyanide. The mixture was incubated for 15 min. at room temp. and then concentrated to 3 to 4 ml using a CentriCell® concentrator (Polysciences) having a 30,000, m.w. cut-off. To a 3.5 ml solution of concentrated BSA-Peptide 39GC was added 0.4 ml of glacial acetic acid. The solution was then applied to a Sephadex® G-75 column (1.5×40 cm) equilibrated with 20% acetic acid and eluted with the same 20% acetic acid solution. Fractions were collected (1.3 ml/tube) and the $A_{280}$ determined for each. The first protein peak was collected and the fractions pooled and 5 volumes of distilled water added. The solution was then frozen in dry ice/acetone, lyophilized, and stored desiccated at 4° C.

The EC deprotected and oxidized Peptide 39GC-BSA was labelled using $^{125}I$ - labelled Bolton-Hunter reagent (obtained from DuPont Chemical Co., Boston, Mass.). A 0.1 mg/ml solution of BSA-Peptide 39GC (EC deprotected and oxidized) was made in 0.1M HEPES, pH 7.0. The organic solvent (benzene) of $^{125}I$-Bolton-Hunter reagent was removed to dryness using a stream of nitrogen, and 15 µl of BSA-Peptide 39GC (EC deprotected and oxidized) solution was added. The mixture was vortexed and incubated overnight at 4.C. Following the incubation, 200 µl of 0.1M HEPES, pH 7.0, containing 0.2% gelatin, was added and mixed. The mixture was applied to a Sephadex® G-25 column (1.5 ×10 cm) equilibrated with 0.1M HEPES, pH 7.0, containing 0.2% gelatin and eluted with the same HEPES buffer (0.5 ml/fraction). The fractions comprising the first radioactive peak were collected and pooled.

Preparation of the Protein A-Polymer Capture Conjugate

The capture conjugate was formed by joining protein A, which binds to the $F_c$ region of most immunoglobulin chains, to A-poly 47 which binds specifically to a cellulose acetate membrane. By reacting the capture conjugate with the sample-signal conjugate mixture, a ternary complex of signal-peptide 39GC/antibody/-protein A-A-poly 47 is formed. The complex is then separated from the reaction mixture by adsorption onto a cellulose acetate membrane.

The conjugation of protein A to A-poly 47 was accomplished as follows. Protein A, 0.5 mg, was dissolved in 2 ml of 0.1M HEPES, pH 7.5. The solution was cooled on ice to keep the temperature below 8° C. The preparation of A-poly 47, a terpolymer of N-isopropylacrylamide: N-acryloxysuccinimide: N-n-butylacrylamide, 60:2.5:40, is prepared according to the procedures as described in co-pending application U.S. Ser. No. 108,485, incorporated by reference herein. A-poly 47, 20 mg dissolved in 100 µl of dry DMF, was added to the protein solution. A-poly 47 immediately flocculates, but slowly goes into solution (A-poly 47 is water soluble below 8° C.). The A-poly 47-protein 5. A was completely dissolved while held on ice, and then incubated overnight at 4° C.

Following overnight incubation, ammonium sulfate precipitation was used to remove unconjugated protein. Ice cold distilled water, 8 ml, was first added to the reaction mixture and then the temperature of the solution was raised to about 22° C. A 2 ml solution of ammonium sulfate, saturated at 4° C. and warmed to room temperature, was added, the solution mixed, and centrifuged for 15 minutes at 3,000 rpm at room temp. in a Beckman benchtop centrifuge Model TJ/6 and the supernatant then removed. Ice cold distilled water, 4 ml, and 1 ml of 0.1M HEPES, pH 7.5, were added to the precipitate and mixed until all of the precipitate dissolved, keeping the solution ice cold throughout. The solution was warmed to room temp. and 1 ml of saturated ammonium sulfate (warmed to room temp.) was added and centrifuged as before. The supernatant was removed and precipitate dissolved as before, and ammonium sulfate added and centrifuged. A total of three washes as described above were performed, and the supernatant of the final wash was removed and 8 ml of ice cold distilled water added to completely dissolve the precipitate.

Hydroxylapatite column chromatography was used to remove unconjugated A-poly 47. A hydroxylapatite column (1×2 cm) was equilibrated with ice cold water and kept at 4° C. The solution from the ammonium sulfate precipitation, cleared of unconjugated protein, was applied to the column, the column washed with two columns of cold water, and the conjugate eluted at 4° C. using ice cold 0.3M potassium phosphate buffer, pH 6.8. The major protein fractions were collected and pooled, and the protein content in the A-poly 47-Protein A conjugate quantitated by a Coomassie blue protein assay.

Assay for Antibodies to HIV-1

The $^{125}I$-Peptide 39-BSA signal conjugate and the A-poly 47-Protein A capture conjugate, prepared as described above were used to determine the presence of antibodies to HIV-1 according to the following protocol.

A solution of 150 µl of PBS containing 1% BSA and $^{125}I$-BSA-Peptide 39GC conjugate (at about $5\times10^5$ cpm) was added to a glass tube, followed by 20 µl of a test serum sample diluted 10 fold in 1% BSA/PBS. To the sample-signal conjugate mixture were added 30 µl of the protein A-A-poly 47 capture conjugate (at about 5 µg of protein A per assay) which solution was mixed and incubated at room temp. for 10 minutes. Following the brief incubation, the assay solution was transferred to a microtiter filtration well (Costar) having a 0.45 μm pore size cellulose acetate membrane on the bottom, and the solution was filtered by vacuum suction. The filters were washed three times with 300 μl of PBS containing 0.05% Tween 20. The 8-well strips were separated into individual wells and each put into a polystyrene tube and counted for radioactivity in a gamma counter.

Figure 2:
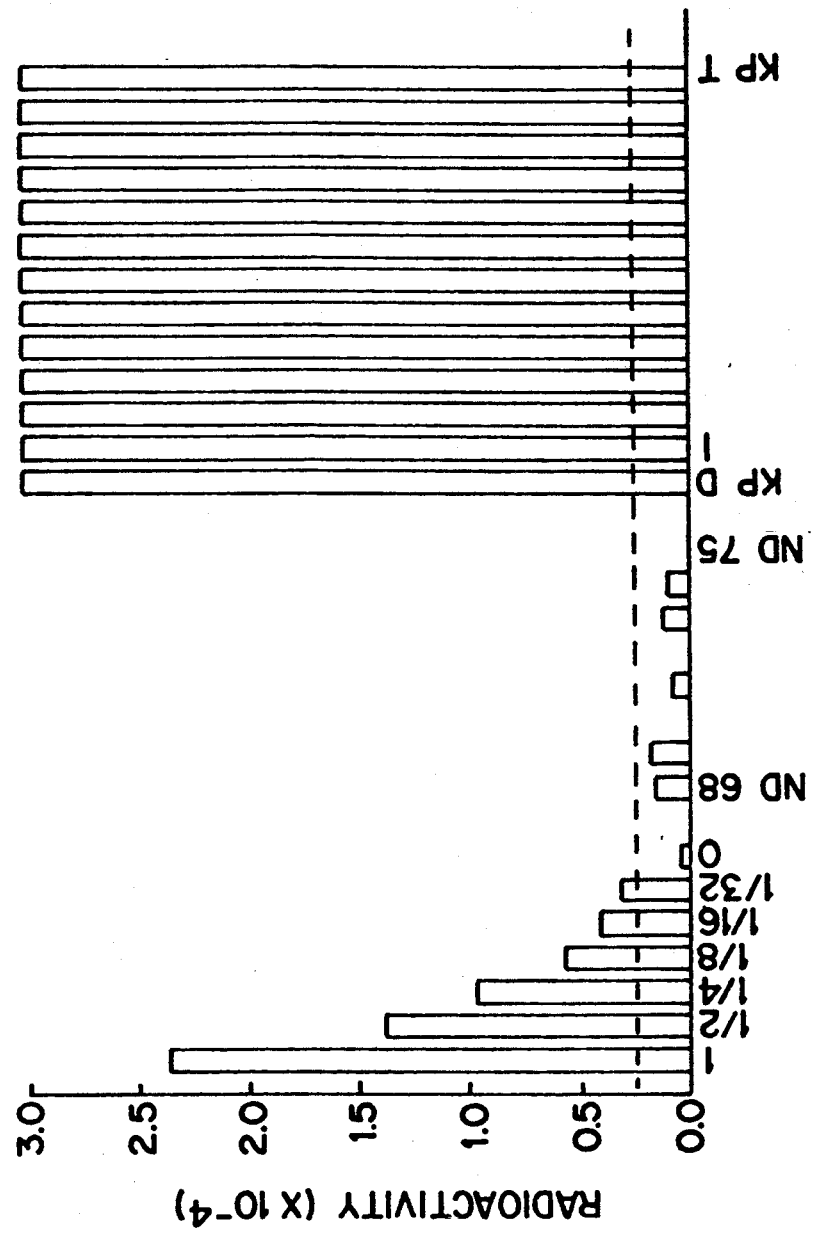
FIG. 2 illustrates the results for assays for antibodies to HIV-1 using positive and negative control sera, normal donors (Nos. 68-75) and known HIV-1 positives (KP D, I-T)

The results for assays using dilutions of an HIV-1 antibody positive control serum from Genetic Systems LAV-EIA kit, out to a final dilution of 1/3200, and 26 normal donors are shown in FIG. 1; similar results for an additional 40 normal donors (Nos. 27-67) were also observed. The results for dilutions of the positive control, a negative control, normal donors (Nos. 68-75), and known HIV-1 positives (KP D, I-T) are shown in FIG. 2. The results show that 75 sera previously confirmed negative for antibodies to HIV-1 tested negative by the present assay, and 14 previously confirmed positives tested positive by this assay.

In subsequent assays the sensitivity of the assays of the present invention was compared to that achievable with a whole virus microELISA (Genetic Systems LAV-EIA) and a rapid filter-based peptide assay. The results of these comparisons are shown in Table I below.

TABLE 1

| Format | Max. Pos. Dil.[1] | Total Inc. | No. Inc. | No. Wash |
|---|---|---|---|---|
| MAC-RIA[2] | 1/32 | 10 min. | 1 | 1 |
| ELISA | ↓ | 150 min. | 3 | 2 |
| Filter | ↓ | 9 min. | 3 | 2 |

[1]Maximum dilution of known positive control serum which yielded positive results.
[2]Membrane affinity concentration-radioimmunoassay.

EXAMPLE II

Assay Using Goat Anti-Human Ig (G+M)-A-poly 47 as Capture Conjugate

The following example describes the use of a capture conjugate having anti-immunoglobulin rather than protein A as the reagent which binds to the immune complexes formed between antigens and antibodies in samples.

The goat anti-human Ig-A-poly 47 conjugate was prepared in a manner similar to the Protein A conjugate, except that 2 mg of affinity purified goat anti-human Ig, rather than 0.5 mg of Protein A, was dissolved in 2 ml of 0.1M HEPES, pH 7.5. The assay procedure using goat anti-human Ig-A-poly 47 capture conjugate was similar to that described in Example I, except that 20 μg of the goat anti-human Ig-A-poly 47 conjugate was added per assay in place of the Protein A-A-poly 47 conjugate.

Figure 3:
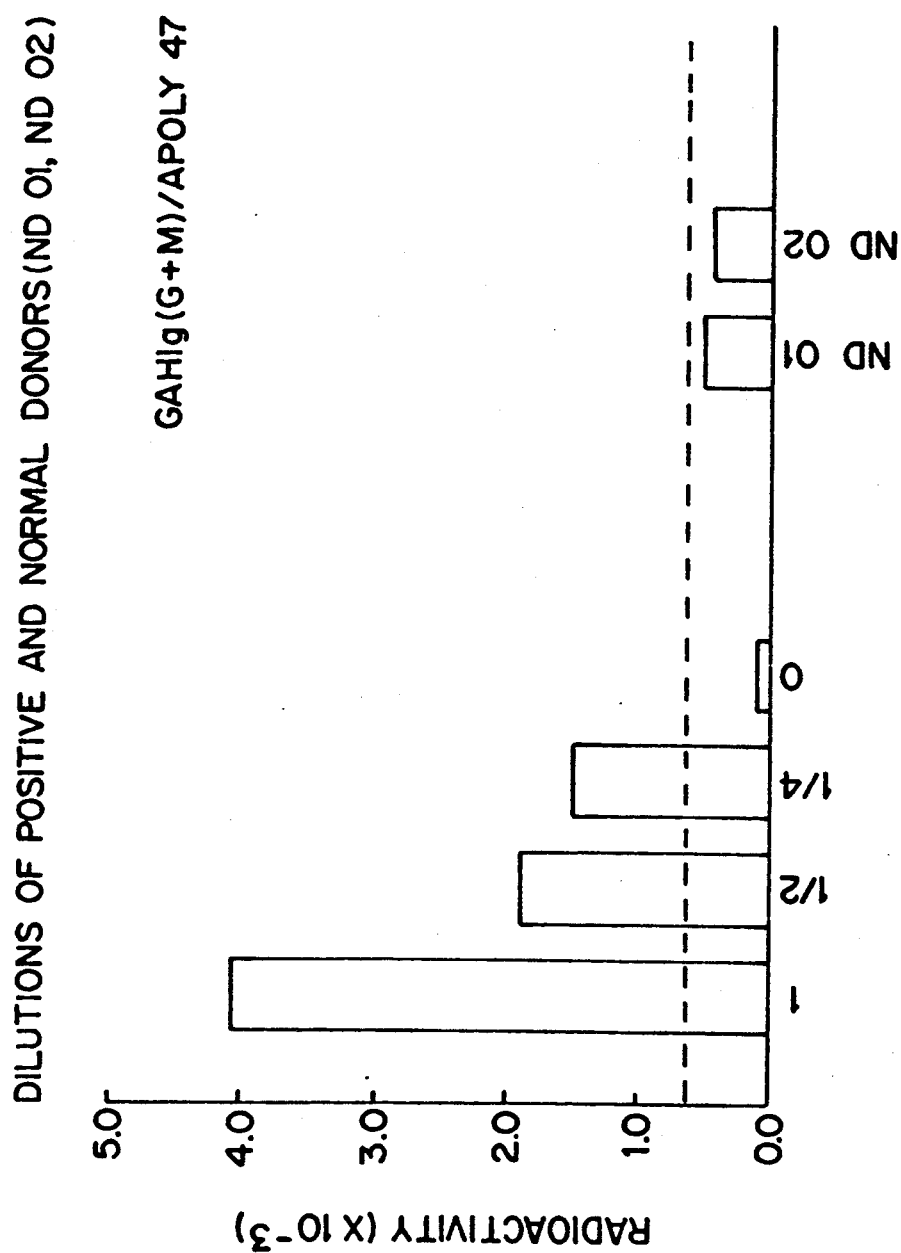
FIG. 3 shows the results of assaying a serial dilution of a HIV-1 positive control serum using a mixture of anti-IgG and anti-IgM antibodies as part of the capture conjugate.

The assay results on a serial dilution of a positive control serum used in Genetic Systems LAV-EIA kit, shown in FIG. 3, demonstrate that this assay format is capable of detecting antibodies to a selected antigen, e.g., HIV-1, in a sensitive and specific manner.

EXAMPLE III

Rapid Enzyme Immunoassay Using a Chemiluminescence Substrate

An enzyme immunoassay for use in the present invention was developed using a chemiluminescence substrate, AMPPD (3-(2'-spiroadamantane)-4-methoxy-4-(3''-phosphoryloxy) phenyl-1,2-dioxetane disodium salt), to provide a signal. This assay showed a sensitivity equal to that obtained with RIA of Example I, and the capacity to detect to a dilution of 1/32 of an HIV-antibody positive control used in an HIV whole virus ELISA kit.

Although the assay format was similar to that described in Example I, several modification in the preparation of reagents were made, which are as follows:

The specimen diluent was 1% BSA/PBS containing 5 mg/ml dextran sulfate (5000 m.w.), 0.1% polyvinylpyrrolidone (PVP) and 15ppm Kathon CG, an antimicrobial preservative (Rohm and Haas, Philadelphia, Pa.). The capture conjugate was 1% BSA/PBS containing 100 μg/ml A-poly 47-Protein A, 10 mM benzamidine HCl and 15 ppm Kathon CG. The signal conjugate, prepared as described further below, was 1% BSA/PBS containing a 1/100 dilution of BSA-39GC-alkaline phosphatase conjugate, 1 mM $MgCl_2$, 10 mM benzamidine HCl and 15 ppm Kathon CG. A wash solution was PBS containing 0.05% Tween-20, 1 mM $MgCl_2$ and 15 ppm Kathon CG. The substrate solution was comprised of 1M 2-Amino-2-methyl-1-propanol buffer, pH 10.2, containing 0.8 mM AMPPD (Tropix, Inc., Boston, Mass.) and a chemiluminescent enhancer (Tropix).

To minimize nonspecific binding, the specimen diluent and the signal conjugate were passed through a 0.2 μm cellulose acetate membrane filter, and the capture conjugate and substrate solution were passed through a 0.4 μm polycarbonate membrane filter.

The BSA-Peptide 39GC conjugate was further conjugated to alkaline phosphatase (AP) using the heterobifunctional reagents, SMCC and N-succinimidyl 3-(2-pyridyldithio)propionate (SPDP). For SMCC labelling of AP, 31 μl of DMF containing 310 μg of sulfo-SMCC (10-fold molar excess) was added to a glass tube containing 10 mg of AP and 2 ml 0.03M triethanolamine (TEA) buffer, pH 8.0. The tube was mixed and immediately sealed with parafilm and incubated for 30 minutes at room temp. For gel filtration of SMCC/AP reaction mixture a Sephadex ® G-25 column (1.5×40 cm) was first equilibrated with 10 mM PBS. The reaction mixture was applied to the column and fractions were collected at 50 drops per tube, each fraction being monitored at $A_{280}$. The fractions comprising the major protein peak were collected and pooled.

To perform the SPDP-labelling of the BSA-Peptide 39GC, 6.16 mg of BSA-peptide 39GC were prepared in 2 ml of 0.1M HEPES, pH 7.0, in a glass tube, to which 29 μl of DMF containing 290 μg of SPDP (10 fold molar excess) were added. The flask was mixed and sealed and incubated for 30 minutes at room temp. To the SPDP-BSA-Peptide 39GC reaction mixture were added 150 μl of 0.02M dithiothreitol (DTT) (in distilled water), which reaction mixture was incubated for 30 minutes at room temp. The mixture was then applied to a Sephadex ® G-25 column (1.5×40 cm, equilibrated with 10 mM PBS) and fractions collected, the fractions being monitored at $A_{280}$ and the major protein peak pooled and then kept on ice.

To conjugate the AP-SMCC and BSA-Peptide 39GC-SH, AP-SMCC was diluted to 1 mg/ml in PBS and added to a BSA-Peptide 39GC-SH solution which was also diluted to 1 mg/ml with PBS. The reaction mixture was incubated for three hours at room temp. and N-ethylmaleimide was added, 180 μl of a solution of 1.25 mg/ml in DMF, to stop the conjugation reaction. The reaction mixture was concentrated with a CentriCell ® to about 3 ml and the concentrate passed through a 0.2 μm membrane to remove insoluble debris. The filtered mixture was applied to a Sephadex ® S-300 column (1.5×80 cm) equilibrated with PBS and the profile monitored at $A_{280}$.

The immunoreactive fraction of BSA-Peptide 39GC-AP conjugation mixture was monitored by micro-ELISA. Microtiter wells were coated with a monoclonal antibody reactive with a gp41 envelope protein of HIV-1 at 10 μg/ml (in carbonate/bicarbonate buffer) and incubated overnight at 4° C. The wells were washed once with 200 μl with 0.05% Tween in PBS and 100 μl of 1% BSA/PBS were added and incubated for 30 minutes at room temp. The wells were washed twice with 200 μl of 0.05% Tween in PBS and a 1/100 dilution (5 μl to 0.5 ml 1% BSA/PBS) of each fraction was added to the wells at 80 μl per well. The reaction mixtures were incubated for 30 minutes, the wells washed three times with 200 μl each of 0.05% Tween/PBS, and 70 μl of the substrate solution (1 mg/ml p-nitrophenyl phosphate in 0.1 M Tris buffer, pH 9.6) added. The mixture was incubated for 30 minutes at room temp. and read at $A_{405}$ in a microELISA reader. The immunoreactive fractions were collected and pooled.

Assay Procedure

Figure 4:
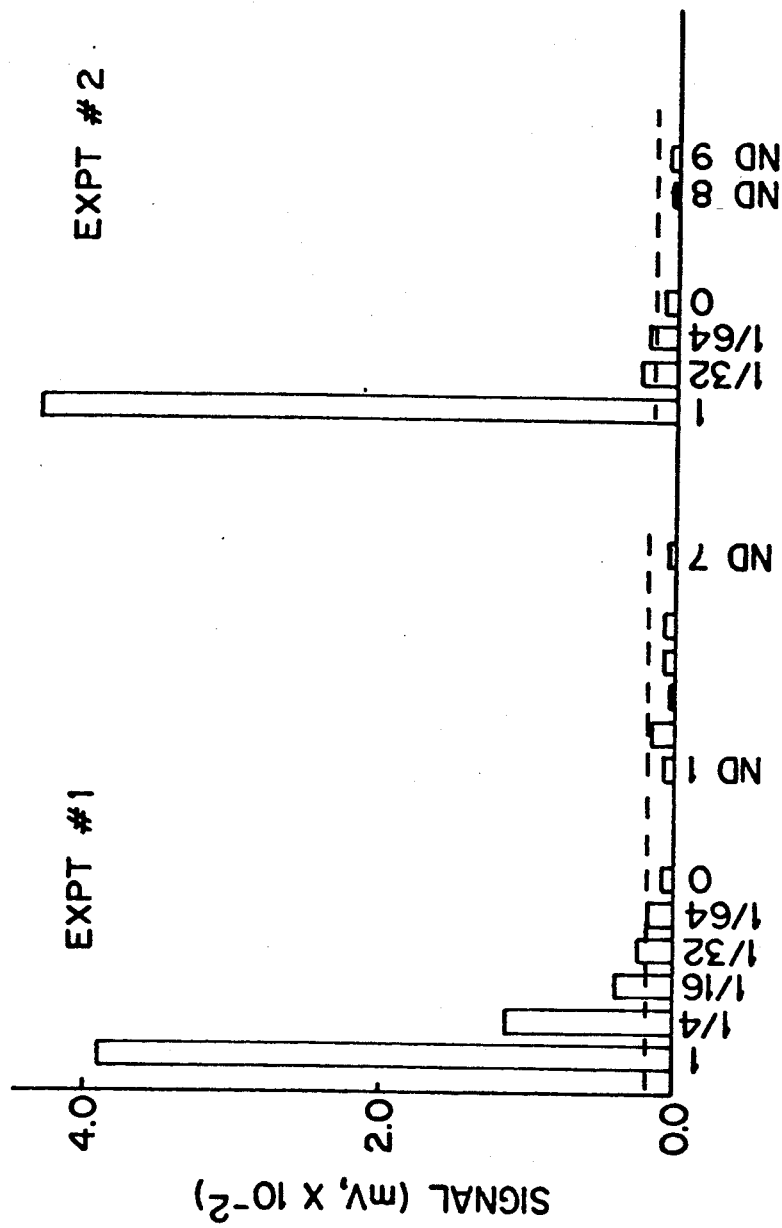
FIG. 4 represents the results obtained with the chemiluminescent substrate AMPPD as signal in assays with dilutions of the positive control serum and nine normal samples.

The ELISA for HIV-1 antibodies using the chemiluminescent AMPPD substrate was performed as follows. The signal conjugate, 60 μl, was added to a glass tube, followed by 40 μl of the sample which had been diluted ten fold with specimen diluent and passed through a 0.45 μm cellulose acetate membrane. The capture conjugate, 100 μl, was added to the tube and the mixture incubated for 15 minutes at room temp. The entire contents were transferred to a microtiter filtration membrane (Costar, 0.45 μm, cellulose acetate), and filtered under vacuum. The membrane was washed six times with 300 μl each of the wash solution, and 100 μl of the substrate solution were added to the well. The substrate was filtered and the individual well was added to the holder on a chemiluminescence reader. The signal was followed for 10 minutes and recorded. The results obtained with the dilutions of the positive control serum and eight normal samples (known negatives), which demonstrate a high level of sensitivity and specificity, are shown in FIG. 4.

EXAMPLE IV

Rapid Chemiluminescence Assay for HIV-1 Antibodies on a Seroconversion Panel

Following the procedures described above in Example III, the chemiluminescence assay was used to test serum samples from a seroconversion panel (a set of serum samples obtained from an individual converting from HIV-1 antibody negative to antibody-positive following exposure to the HIV virus). The results were obtained by Western blot, a rapid peptide assay as described in copending application 07/532,429 and from seven commercially available enzyme immunoassays licensed by the US FDA. The results are shown below in Table II.

TABLE II

| Serum Sample # | Western Blot | Rapid Peptide Assay +/− | Licensed EIAs | Chemiluminescence Assay +/−* |
|---|---|---|---|---|
| 20 | − | − | − | 0/7 | 0.43 | − |

TABLE II-continued

| Serum Sample # | Western Blot | Rapid Peptide Assay +/− | Licensed EIAs | Chemiluminescence Assay +/−* |
|---|---|---|---|---|
| 21 | − | − | − | 0/7 | 0.63 | − |
| 22 | + | Trace | + | 0/7 | 1.32 | + |
| 23 | + | 1+ | + | 1/7 | 5.62 | + |
| 24 | + | 1+ | + | 1/7 | 5.29 | + |

*Cut-off = 1.0 The numbers represent luminescence values detected by a Dynatech MicroELISA luminometer.

The above results show the affinity-based chemiluminescence assay to be not only rapid, but also sensitive enough to detect all samples which tested positive by Western blot and EIA, emphasizing the high degree of sensitivity present in this rapid assay format.

EXAMPLE V

Use of Rapid Chemiluminescence Assay to Detect HIV-1 Antibodies in Urine

Using the procedures described in Example IV above, the rapid chemiluminescence enzyme immunoassay was used to test for sensitivity for antibodies in urine. Six urine samples, which were confirmed positive by a commercially available HIV-1 EIA test and a Western blot test, were tested using the chemiluminescence assay described above in Example IV, in addition to a rapid peptide assay. The rapid peptide assay was used as a reference assay for the peptide-based antigen system. As shown in Table III below, all six urine samples tested positive by the chemiluminescence assay. This again confirms that even though in a rapid assay format, the assay of the present invention is sensitive enough to detect all samples which tested positive by the conventionally used Western blot and whole virus EIA.

TABLE III

Rapid Chemiluminescence EIA for HIV-1 Antibodies on Urine Samples

| Urine Sample No. | Western Blot | LAV EIA[a] +/− | HIV-1 Peptide[b] Assay +/− | Chemiluminescent[c] Assay +/− |
|---|---|---|---|---|
| 010N | + | 1.467 | + | Trace | + | 0.80 | + |
| 015N | + | 2.185 | + | − | − | 0.80 | + |
| 017N | + | 0.999 | + | 0.5+ | + | 2.52 | + |
| 005B | + | 0.660 | + | − | − | 1.72 | + |
| 009B | + | 2.349 | + | 1.0+ | + | 4.34 | + |
| 010B | + | 0.890 | + | − | − | 0.41 | + |
| ND[d] | − | 0.024 | − | − | − | 0.05 | − |

[a]All the values are O.D. at 450 nm using a Biotech microELISA reader; cutoff at 0.2.
[b]The sample was diluted two (2)-fold with the specimen diluent and then used in the assay.
[c]All the values are luminescence values detected by a Dynatech mciroELISA luminometer; cutoff = 0.10.
[d]Normal Donor Although the foregoing invention has been described in some detail by way of illustration and example for purposes of clarity of understanding, it will be apparent that certain changes and modifications may be practiced within the scope of the appended claims.

What is claimed is:

1. A method for determining the presence of an HIV analyte of interest in a fluid sample, which comprises:
   incubating in the substantial absence of unconjugated polymer a sample suspected of containing the HIV analyte of interest with (i) a labelled conjugate which comprises a first reactant conjugated to a label capable of providing a detectable signal, said first reactant being capable of specifically binding with the analyte and (ii) a second conjugate which comprises a second reactant that binds to the analyte, and a polymer selected from a group consisting of N-alkylacrylamides, N-arylacrylamides, alkyl acrylates, aryl acrylates, and combinations thereof conjugated to said second reactant, thereby forming a reaction mixture;

contacting the reaction mixture with a solid phase which comprises a cellulose ester; and measuring the amount of label bound to the solid phase and therefrom determining the presence of said analyte.

2. The method of claim 1, wherein the analyte comprises antibodies to HIV.

3. The method of claim 2, wherein the antibodies are to HIV-1.

4. The method of claim 2, wherein the antibodies are to HIV-2.

5. The method of claim 2, wherein the first reactant which specifically binds with the antibodies to HIV is a synthetic peptide, purified native antigen, or recombinant protein.

6. The method of claim 5, wherein the first reactant is coupled to a carrier.

7. The method of claim 6, wherein the carrier is a soluble protein.

8. The method of claim 1, wherein the label is a fluorescer, radionuclide, chemiluminescer, enzyme or dye.

9. The method of claim 8, wherein the label is $^{125}I$.

10. The method of claim 8, wherein the label is 3-(2'-spiroadamantane)-4-methoxy-4-(3''-phosphoryloxy)-phenyl-1,2-dioxetane, 3-(2'-spiroadamantane)-4-methoxy-4-(3''-$\beta$-D-galactopyranosyloxy)phenyl-1,2-dioxetane, luminol, isoluminol, or firefly luciferin.

11. The method of claim 1, wherein the first and second reactants are different.

12. The method of claim 2, wherein the second reactant that binds to the antibodies is protein A or an anti-immunoglobulin antibody.

13. The method of claim 12, wherein the anti-immunoglobulin antibodies are anti-human immunoglobulin.

14. The method of claim 13, wherein the anti-human immunoglobulin antibodies are anti-human IgG and anti-human IgM.

15. The method of claim 1, further comprising at least one wash step between the steps of contacting and measuring.

16. The method of claim 1, wherein the solid phase is cellulose acetate.

17. The method of claim 1, wherein the polymer having a selected affinity for the solid phase is a terpolymer of N-isopropylacrylamide: N-acryloxysuccinimide: N-n-butylacrylamide.

18. The method of claim 1, wherein the fluid sample is blood, blood serum, blood plasma, saliva or urine.

19. A method for determining the presence of an hepatitis B virus antigen of interest in a fluid sample, which comprises:

incubating in the substantial absence of unconjugated polymer a sample suspected of containing the hepatitis B antigen with (i) a labelled conjugate which comprises a first antibody that specifically binds with the hepatitis antigen conjugated to a label capable of providing a detectable signal, and (ii) a second conjugate which comprises a second antibody that binds to the hepatitis antigen conjugated to a polymer selected from a group consisting of N-alkylacrylamides, N-arylacrylamides, alkyl acrylates, aryl acrylates, and combinations thereof, thereby forming a reaction mixture;

contacting the reaction mixture with a solid phase which comprises a cellulose ester; and measuring the amount of label bound to the solid phase and therefore determining the presence of said antigen.

20. A method for determining the presence of an analyte of interest in a fluid sample, which comprises:

incubating in the substantial absence of unconjugated polymer a sample suspected of containing the analyte of interest with (i) a labelled conjugate which comprises a first reactant that specifically binds with the analyte conjugated to a label capable of providing a detectable signal, and (ii) a second conjugate which comprises a second reactant that binds to the analyte conjugated to biotin, thereby forming a reaction mixture;

admixing in the reaction mixture a third conjugated which comprises avidin conjugated to a polymer selected from a group consisting of N-alkylacrylamides, N-arylacrylamides, alkyl acrylates, aryl acrylates, and combinations thereof, thereby forming an admixture;

contacting the admixture with a solid phase which comprises a cellulose ester; and measuring the amount of label bound to the solid phase and therefrom determining the presence of said analyte.

21. The method of claim 1, wherein the cellulose ester is cellulose acetate.

* * * * *